(12) United States Patent
Oster

(10) Patent No.: US 9,775,970 B2
(45) Date of Patent: Oct. 3, 2017

(54) APPARATUS AND METHODS FACILITATING THE REPOSITIONING OF IMPLANTED MEDICAL DEVICES

(71) Applicant: Medtronic, Inc., Minneapolis, MN (US)

(72) Inventor: Daniel C. Oster, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 226 days.

(21) Appl. No.: 14/184,141

(22) Filed: Feb. 19, 2014

(65) Prior Publication Data

US 2014/0257337 A1 Sep. 11, 2014

Related U.S. Application Data

(60) Provisional application No. 61/776,303, filed on Mar. 11, 2013.

(51) Int. Cl.
*A61M 25/02* (2006.01)
*A61M 25/06* (2006.01)

(52) U.S. Cl.
CPC ..... *A61M 25/02* (2013.01); *A61M 2025/0675* (2013.01)

(58) Field of Classification Search
CPC .......... A61M 25/02; A61M 2025/0293; A61M 2025/0675; A61N 1/05; A61N 1/057; A61N 1/0558; A61N 2001/0578; A61N 2001/058; A61N 2001/0582; A61B 17/0467; A61B 17/320016; A61B 2017/0411; A61F 2/95; A61F 2002/9517; A61F 2002/9534; H02G 1/1229; H02G 1/1251; H02G 1/126; H02G 1/1217
See application file for complete search history.

(56) References Cited

U.S. PATENT DOCUMENTS 2,120,398 A * 6/1938 Edwards .............. H02G 1/1229 30/90.6
2,452,734 A * 11/1948 Costelow ............. H02G 1/1229 30/90.7

(Continued)

OTHER PUBLICATIONS

PCT/US2014/017133: Search Report and Written Opinion dated Apr. 7, 2014.

*Primary Examiner* — David C Eastwood
(74) *Attorney, Agent, or Firm* — Mueting, Raasch & Gebhardt, P.A.

(57) ABSTRACT

Dislodging an anchor sleeve from an implanted device may be accomplished with a tool that includes a support portion and a sleeve dislodging element, wherein a collar of the support portion engages a distal end of the anchor sleeve while the dislodging element, positioned at a proximal end of the sleeve, is moved toward the collar to dislodge the anchor sleeve. The tool preferably includes a handle member held in sliding engagement with a base member, for example, by a snap-fit, wherein the support portion is part of the handle member, and a distal segment of the base member is terminated by the dislodging element. A tool kit may include a plurality of base members, each one including a different type of dislodging element, from which an operator may select for snap-fitting to a handle member of the kit.

13 Claims, 6 Drawing Sheets

(56) References Cited

U.S. PATENT DOCUMENTS

| | | | | |
|---|---|---|---|---|
| 2,683,308 | A * | 7/1954 | Cook, Jr. | H02G 1/1217 30/91.1 |
| 3,599,514 | A * | 8/1971 | Fornkahl | H02G 1/1229 30/90.6 |
| 3,832,767 | A * | 9/1974 | Petree | H02G 1/12 29/564.4 |
| 4,063,343 | A * | 12/1977 | Reymond | G02B 6/245 29/867 |
| 4,117,749 | A * | 10/1978 | Economu | H02G 1/1229 30/90.6 |
| 4,306,562 | A | 12/1981 | Osborne | |
| 4,402,685 | A | 9/1983 | Bühler et al. | |
| 4,509,257 | A * | 4/1985 | Moriyama | H02G 1/1204 29/825 |
| 4,646,755 | A * | 3/1987 | Kane | A61N 1/057 607/126 |
| 4,776,846 | A | 10/1988 | Wells | |
| 4,947,549 | A * | 8/1990 | Genovese | G02B 6/245 30/90.8 |
| 5,195,978 | A | 3/1993 | Schiffer | |
| 5,335,671 | A * | 8/1994 | Clement | A61M 39/223 600/566 |
| 5,338,292 | A * | 8/1994 | Clement | A61M 39/223 604/22 |
| 5,409,013 | A * | 4/1995 | Clement | A61B 10/04 600/566 |
| 5,409,469 | A | 4/1995 | Schaerf | |
| 5,584,874 | A | 12/1996 | Rugland et al. | |
| 5,601,568 | A * | 2/1997 | Chevillon | A61F 2/01 606/108 |
| 5,683,446 | A | 11/1997 | Gates | |
| 5,713,867 | A | 2/1998 | Morris | |
| 5,752,937 | A | 5/1998 | Otten et al. | |
| 5,873,886 | A * | 2/1999 | Larsen | A61B 10/04 606/159 |
| 5,893,862 | A * | 4/1999 | Pratt | A61F 9/00763 604/22 |
| 5,913,866 | A * | 6/1999 | Ginn | A61B 17/00008 606/170 |
| 6,007,554 | A * | 12/1999 | Van Ess | A61B 17/320016 604/22 |
| 6,554,802 | B1 | 4/2003 | Pearson et al. | |
| 6,884,240 | B1 * | 4/2005 | Dykes | A61B 17/3211 30/162 |
| 6,887,417 | B1 | 5/2005 | Gawreluk et al. | |
| 2003/0125619 | A1 * | 7/2003 | Manning | A61M 25/0668 600/435 |
| 2003/0130598 | A1 * | 7/2003 | Manning | A61B 5/0422 600/585 |
| 2003/0188432 | A1 * | 10/2003 | Temple | H02G 1/1229 30/90.6 |
| 2004/0059348 | A1 * | 3/2004 | Geske | A61B 17/22031 606/129 |
| 2005/0182435 | A1 * | 8/2005 | Andrews | A61M 25/00 606/172 |
| 2006/0167417 | A1 * | 7/2006 | Kratz | A61M 25/0668 604/164.05 |
| 2008/0108972 | A1 * | 5/2008 | Andrews | A61M 25/00 604/523 |
| 2008/0154293 | A1 * | 6/2008 | Taylor | A61B 17/32053 606/170 |
| 2009/0054840 | A1 | 2/2009 | Drake et al. | |
| 2010/0024604 | A1 * | 2/2010 | Nelson | H02G 1/1229 81/9.4 |
| 2010/0082000 | A1 | 4/2010 | Honeck et al. | |
| 2010/0228262 | A1 * | 9/2010 | Cully | A61N 1/05 606/129 |
| 2011/0046710 | A1 * | 2/2011 | Mangiardi | A61B 17/12022 623/1.11 |
| 2012/0197264 | A1 * | 8/2012 | Silverberg | A61B 17/0467 606/129 |
| 2012/0197367 | A1 * | 8/2012 | Olson | A61N 1/0558 607/116 |
| 2012/0215071 | A1 * | 8/2012 | Mahlin | A61B 5/0215 600/208 |
| 2014/0066709 | A1 * | 3/2014 | Mirza | A61B 17/320036 600/106 |
| 2014/0257318 | A1 * | 9/2014 | Behymer | A61M 25/02 606/108 |
| 2015/0005857 | A1 * | 1/2015 | Kern | A61N 1/05 607/116 |

* cited by examiner

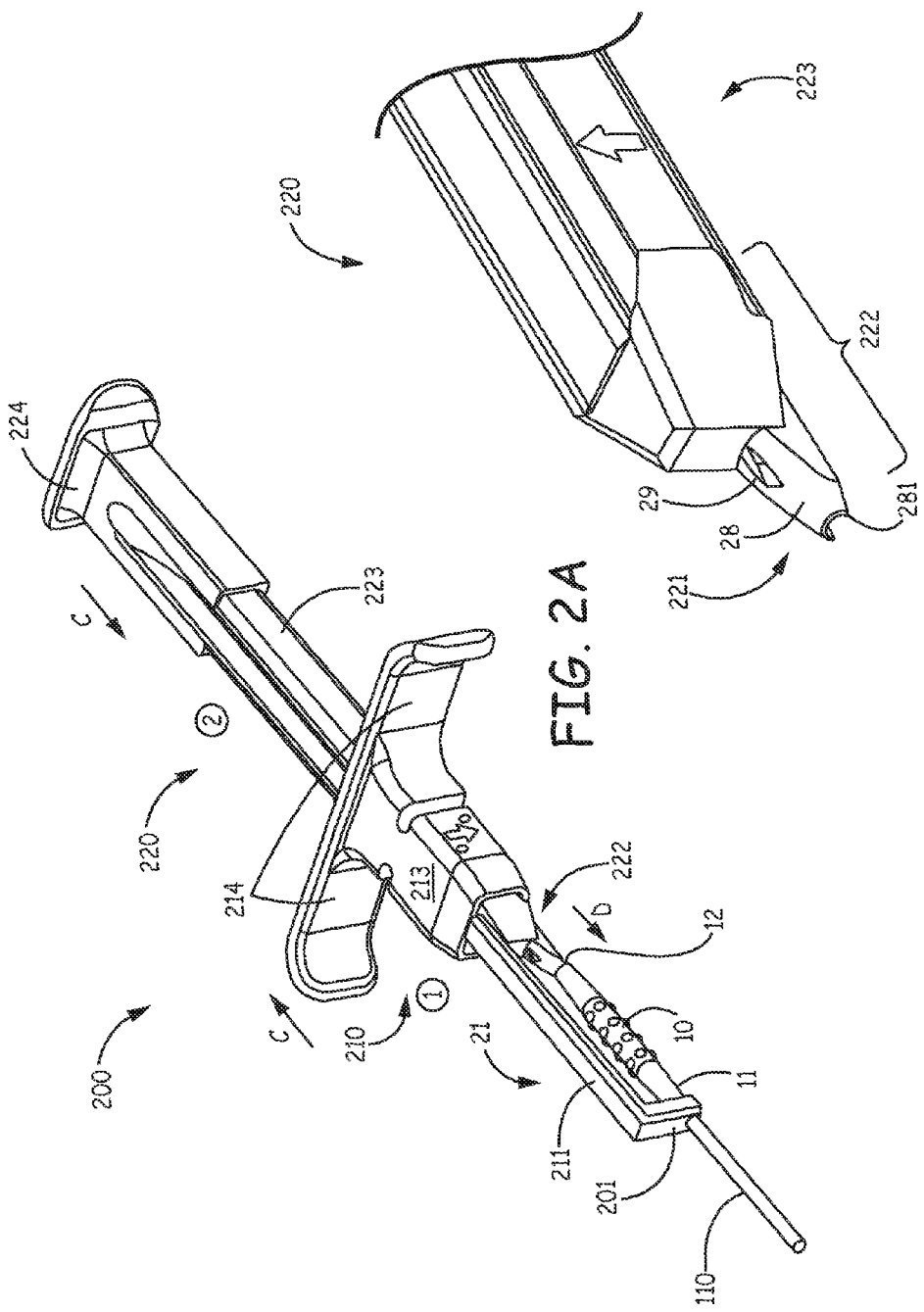

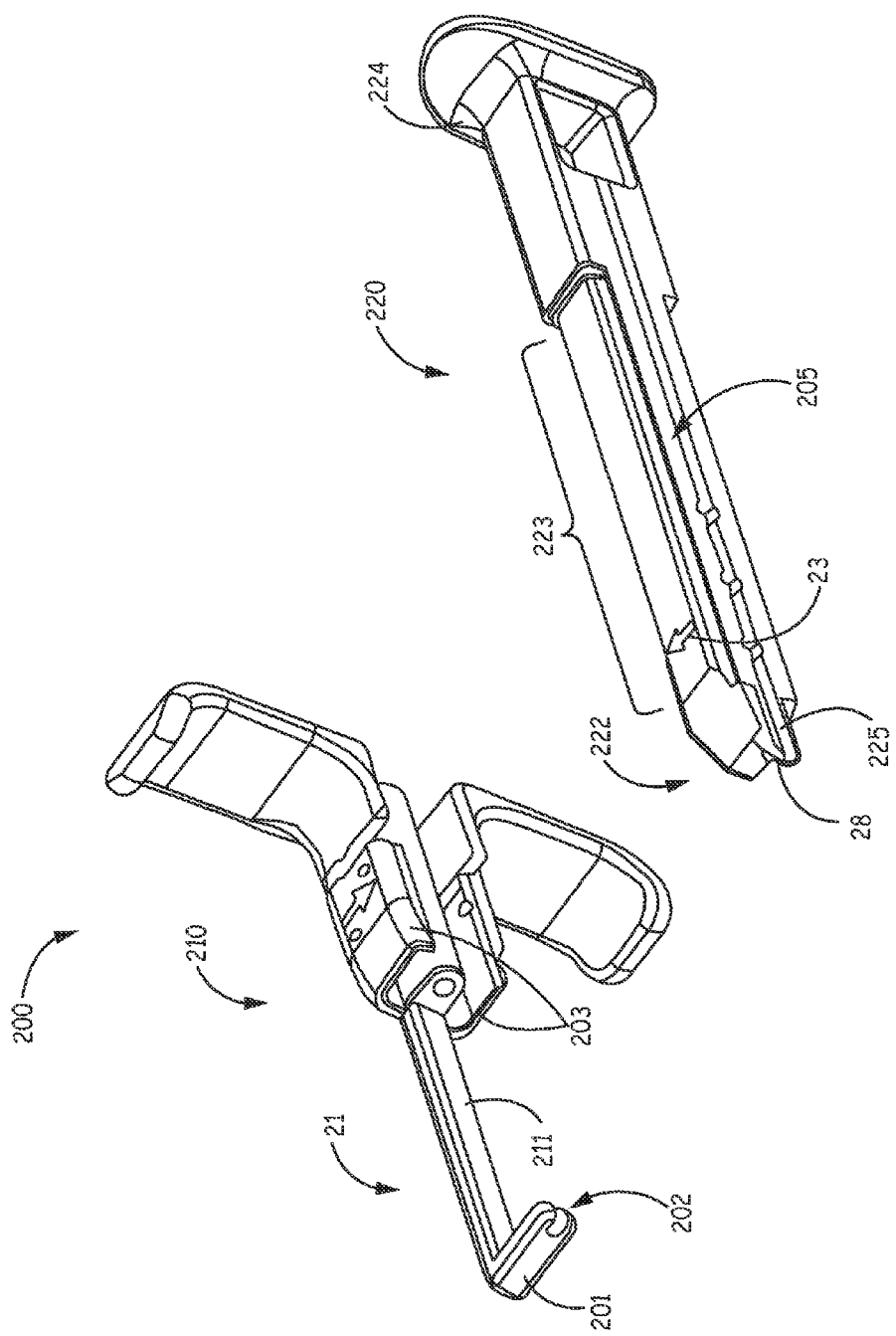

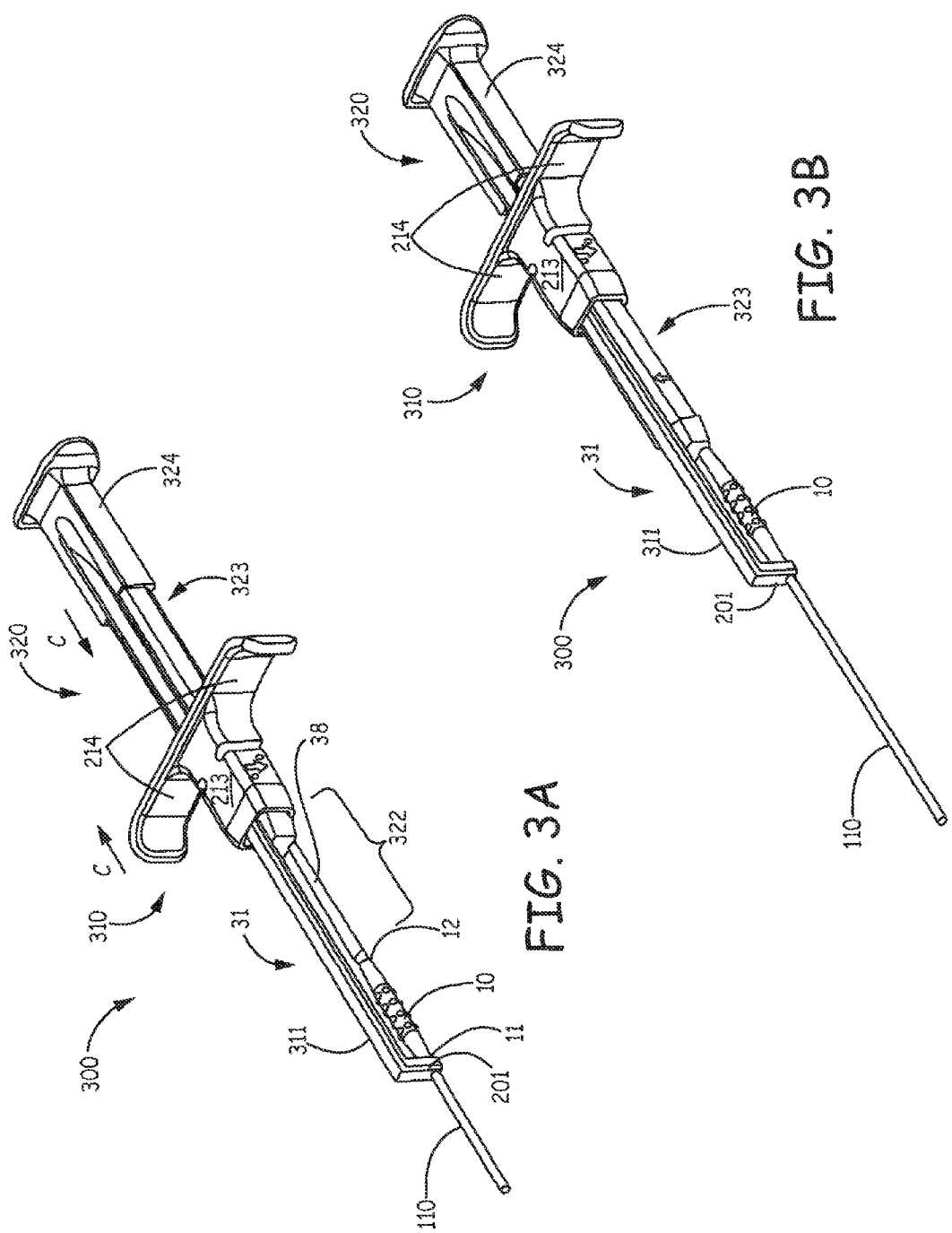

APPARATUS AND METHODS FACILITATING THE REPOSITIONING OF IMPLANTED MEDICAL DEVICES

TECHNICAL FIELD

The present disclosure is related to implantable medical devices, and more particularly to apparatus and methods that facilitate repositioning the devices after initial implant.

BACKGROUND

A variety of elongate implantable medical devices, for example, drug delivery catheters and medical electrical leads, are known in the art, for example, to couple a therapy delivery generator and/or diagnostic devices to a target site within a body of a patient, for example, in the spinal column or in any of a number of internal organs. Those skilled in the art are familiar with apparatus and methods for anchoring these implanted devices. FIG. 1 is a schematic depicting a surgical incision site 12 through which an exemplary elongate medical device 110 has been implanted. FIG. 1 illustrates a length of device 110 extending proximally out from site 12 and an anchor sleeve 10 surrounding a body of device 110, for example, with a relatively tight, interference fit, to facilitate anchoring of device 110 to subcutaneous tissue 14, for example, via sutures (not shown) tied thereabout and sewn into the tissue 14. If it becomes necessary to reposition the anchored implanted device 110, the sutures can be cut, but it may also be desirable to remove and replace anchor sleeve 10 with a new anchor sleeve, or to reposition anchor sleeve 10, at a new location along the body of device 110, and then to re-anchor the repositioned device.

BRIEF DESCRIPTION OF THE DRAWINGS

The following drawings are illustrative of particular embodiments of the present disclosure and therefore do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 2A is a perspective view of an exemplary tool positioned to dislodge an anchor sleeve from around a body of an implanted medical device, according to some exemplary embodiments;

FIG. 2B is an enlarged view of a portion of the exemplary tool shown in FIG. 2A; FIG. 2C is an exploded perspective view of the exemplary tool, according to some exemplary embodiments;

FIG. 3A is a perspective view of another exemplary tool positioned to dislodge the anchor sleeve, according to some alternate exemplary embodiments;

FIG. 3B is a perspective view of the exemplary tool shown in FIG. 3A having dislodged the anchor sleeve, according to some exemplary methods;

DETAILED DESCRIPTION

Figure 1:
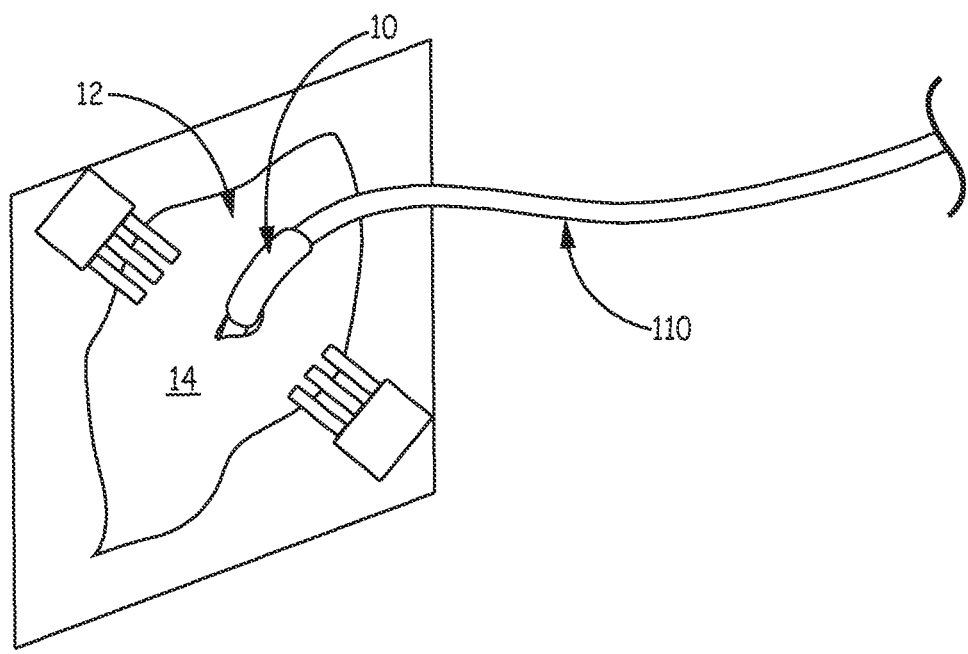
FIG. 1 is a schematic depicting a surgical incision site through which an exemplary elongate medical device has been implanted.

The following detailed description is exemplary in nature and is not intended to limit the scope, applicability, or configuration of the disclosure in any way. Rather, the following description provides practical examples, and after reading the present disclosure, those skilled in the art will recognize that some of the examples may have suitable alternatives.

FIG. 2A is a perspective view of an exemplary tool 200 configured to dislodge anchor sleeve 10 from around the body of implantable device 110, for example, when, after initial implant and anchoring of device 110, an operator desires to reposition device 110. FIG. 2A illustrates tool 200 including a handle member 210 and a base member 220, wherein a body portion 213 of handle member 210 holds base member 220 in sliding engagement, for example, by opposing gripping arms 203, which are best seen in FIG. 2C, fitted around a rail segment 223 of base member 220. FIG. 2A further illustrates a support portion 21 of handle member 210 including an elongate arm 211, which extends distally from body portion 213, and a collar 201, which terminates a distal end of arm 211, for engaging a distal end 11 of anchor sleeve 10, while a sleeve dislodging element 221 of base member 220, which is best seen in FIG. 2B, dislodges anchor sleeve 10.

FIG. 2B is an enlarged view of a distal segment 222 of base member 220. FIG. 2B illustrates dislodging element 221 terminating distal segment 222, and including a blade 29 and a shroud structure 28, which supports blade 29. Shroud structure 28 is shown including a tapered leading edge 281 to slide between the body of device 110 and anchor sleeve 10, when inserted therebetween at a proximal end 12 of sleeve 10, so that blade 29, which is recessed from leading edge 281, can cut through a wall of anchor sleeve 10, per the dashed double-line arrow of FIG. 2A, in order to dislodge, or remove sleeve 10 from around the body of device 110. The insertion of leading edge 281 between sleeve 10 and device 110 stretches sleeve 10, which is formed from an elastic material, such as medical grade silicone rubber, away from device 110 and into contact with blade 29. With further reference to FIG. 2A, in conjunction with FIG. 2C, collar 201 is sized to receive the body of device 110 therein, for example, by pressing the body through an opening 202 of collar 201, and collar 201 is spaced apart from sleeve dislodging element 221 by a distance to accommodates a length of anchoring sleeve 10 between collar 201 and dislodging element 221, when handle member 210 is in a first position 1, relative to base member 220, as illustrated. According to the illustrated embodiment, collar 201 of handle member 210 engages distal end 11 of sleeve 10, while dislodging element 221 is moved, per arrow D, by pushing base member 220, relative to handle member 210; and this engagement of collar 201 stabilizes anchor sleeve 10 for the advance of blade 29 through the wall thereof.

FIG. 2A further illustrates handle member 210 including at least one laterally extending tab element 214, which is configured for engagement by one or more fingers of a hand, and a proximal end 224 of base member 220, which is configured for simultaneous engagement of another portion of the hand, for example, a thumb. The engagement of the hand, per arrows C, to pull handle member 210 while pushing base member 220, moves handle member 210 to a second position 2, relative to base member 220, while collar 201 engages sleeve 10, and blade 29 moves toward collar 201, while cutting through the wall of sleeve 10. FIG. 2C illustrates shroud structure 28 formed around an open channel 225 that extends proximally along a side 205 of base member 220, which side 205 is opposite a side on which arm 211 of support portion 21 extends, when body portion 213 of handle member 210 holds base member 220 in sliding engagement, as shown in FIG. 2A. A length of the body of device 110 may extend within the base portion of channel 225 while tool 200 is manipulated to dislodge sleeve 10. According to an exemplary embodiment, body portion 213, arm 211, and collar 201 of handle member 210, and all but blade 29 of base member 220 are formed, for example, by injection molding, from a polycarbonate material; and blade 29 of base member 220 is formed from stainless steel.

According to some exemplary embodiments and methods, a package or kit includes handle member 210 and base member 220 as separate components to be assembled together by the operator. FIG. 2C further illustrates rail segment 223 of base member 220 including a marked portion 23 located in proximity to distal segment 222, wherein marked portion 23 facilitates alignment and orientation of base member 220 with gripping arms 203 of handle member 210 for a snap-fit of base member 220 with handle member 210 to form tool 200. The snap-fit configuration of members 210, 220 accommodates modular assemblies of alternative types of base members and handle members, for example, included in a kit 400, which is described below in conjunction with FIG. 4.

Figure 3C:
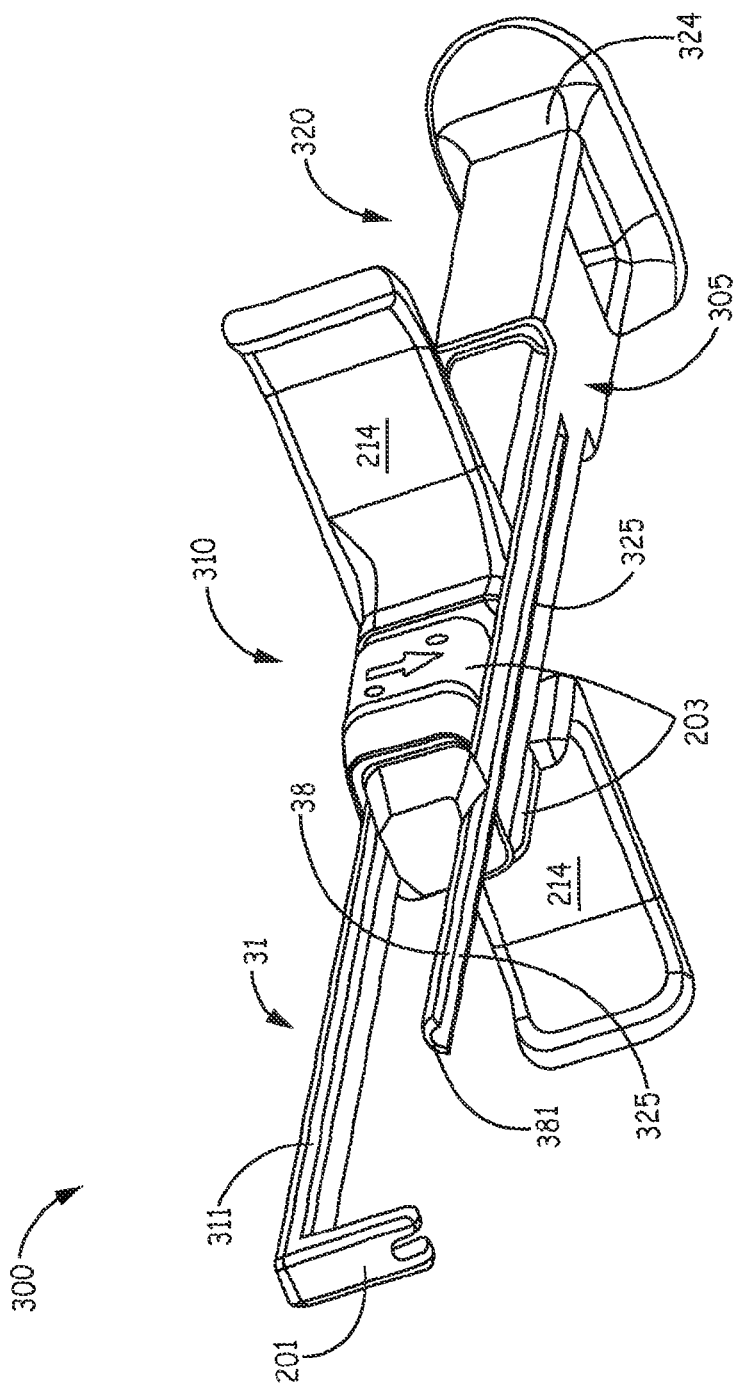
FIG. 3C is another perspective view of the exemplary tool shown in FIGS. 3A-B, according to some exemplary embodiments.

FIG. 3A is a perspective view of another type of exemplary tool 300 positioned to dislodge anchor sleeve 10 from around the body of device 110, and FIG. 3B is a perspective view of tool 300 having dislodged sleeve 10, according to some embodiments and methods. FIGS. 3A-B illustrate tool 300 including a handle member 310 and a base member 320, wherein handle member 310, like handle member 210, includes body portion 213, which holds base member 320 in sliding engagement therewith. A support portion 31 of handle member 310 is shown including collar 201, like support member 21, and an elongate arm 311, which extends distally from body portion 213 to be terminated at a distal end by collar 201. A distal segment 322 of base member 320 is shown terminated by a sleeve dislodging element in the form of an elongate shroud structure 38. With reference to FIG. 3C, shroud structure 38, which is configured for insertion in between anchor sleeve 10 and the body of device 110, along a majority of a length of sleeve 10, includes a tapered leading edge 381. FIG. 3C further illustrates shroud structure 38 formed around an open channel 325, that extends proximally along a side 305 of base member 320, similar to channel 225 of base member 220. Shroud structure 38 is preferably formed from polycarbonate, but may be formed from stainless steel, in which case an outer perimeter surface thereof preferably includes a lubricious coating, such as a fluoropolymer coating. Handle member 310 and a remainder of base member 320 may be constructed from the same exemplary materials indicated above for handle member 210 and base member 220.

With reference to FIG. 3A, a length of arm 311 of support portion 31 of handle member 310 is such that, when collar 201 of support portion 31 is initially positioned around the body of device 110, adjacent to distal end 11 of anchoring sleeve 10, tapered leading edge 381 of sleeve dislodging element/elongate shroud structure 38 is located adjacent to proximal end 12 of sleeve 10. According to the illustrated embodiment, collar 201 engages distal end 11 of anchor sleeve 10 to stabilize sleeve 10, while the operator pushes base member 320, relative to handle member 310, to insert and advance sleeve dislodging element/elongate shroud structure 38 in between sleeve 10 and the body of device 110 and toward collar 201, thereby dislodging sleeve 10. Tool 300 may be engaged by a hand in a similar fashion to that described for tool 200, and the engagement of the hand, per arrows C, moves handle member 310 and base member 320, relative to one another, from the positions thereof shown in FIG. 3A to those shown in FIG. 3B. This relative movement inserts and slides dislodging element/shroud structure 38 in between anchor sleeve 10 and the body of device 110 until a majority of anchor sleeve 10, which is formed from an elastic material, such as silicone rubber, stretches and extends around shroud structure 38, as illustrated in FIG. 3B.

Figure 4:
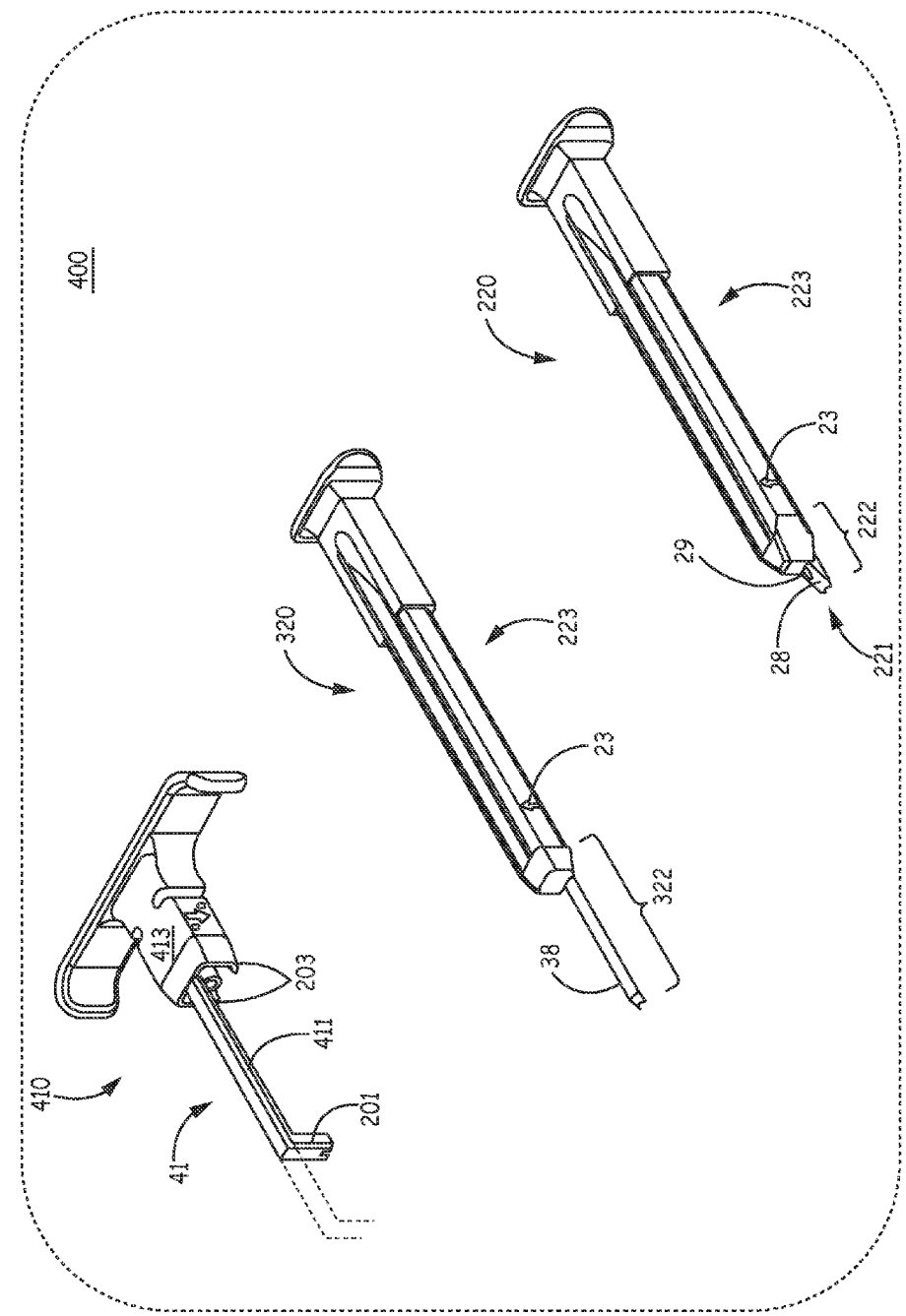
FIG. 4 is a perspective view of members of an exemplary kit, according to some exemplary embodiments.

FIG. 4 is a perspective view of members of an exemplary kit 400, according to some exemplary embodiments. FIG. 4 illustrates kit 400 including both of the above-described base members 220, 320, so that the operator has an option to select between the two types of dislodging elements, blade 29 or elongate shroud structure 38. FIG. 4 further illustrates kit 400 including a handle member 410, which is similar to the above-described handle members 210, 310, except that a support portion 41 of handle 410 is adjustable to accommodate either one of base members 220, 320. According to the illustrated embodiment, an arm 411 of support portion 41 has an adjustable length between a first length, to accommodate dislodging element 221 of base member 220, and a second length (shown with dashed lines) to accommodate dislodging element 38 of base member 320. With reference back to FIG. 2A, the first length of arm 411 is approximately equal to the length of anchor sleeve 10 plus a length of distal segment 222 of base member 220, and, with reference back to FIG. 3A, the second length of arm 411 is approximately equal to the length of anchor sleeve 10 plus a length of distal segment 320 of base member 320. According to an exemplary embodiment, arm 411 is adjustable via a telescoping configuration with a body portion 413 of handle member 410, wherein a detent-like locking feature may formed within body portion 413 to secure support portion 41 at each of the first and second arm lengths. With further reference to FIG. 4, it should be noted that body portion 413 of handle member 410 preferably includes opposing gripping arms 203 configured to receive either of base members 220, 320 therebetween in a snap-fit, as described above; and marked portion 23 of each base member 220, 320 facilitates the proper alignment and orientation of gripping arms 203 for making the snap-fit assembly.

In the foregoing detailed description, the disclosure has been described with reference to specific embodiments. However, it may be appreciated that various modifications and changes can be made without departing from the scope of the disclosure as set forth in the appended claims. Furthermore, tools and kits for forming the tools, which include various combinations of features described above in conjunction with the specific embodiments, are within the scope of the present disclosure, for example, according to the following 11 statements that disclose features or combinations of features in exemplary embodiments:

1. In some exemplary embodiments, a tool for dislodging an anchor sleeve from around a body of an implanted elongate medical device, the tool comprises: a handle member including a body portion and a support portion, the support portion including an elongate arm extending distally from the body portion, and a collar terminating a distal end of the arm, the collar being sized to receive the body of the medical device therein and to engage a distal end of the anchor sleeve; and an elongate base member held in sliding engagement with the body portion of the handle member, the base member including a distal segment and a proximal end, the distal segment being terminated by a sleeve dislodging element, the sleeve dislodging element being directed toward the collar of the support portion of the handle member; wherein the handle member slides along the base member between a first position, in proximity to the distal segment of the base member, and a second position, in proximity to the proximal end of the base member; the collar of the support portion of the handle member is spaced distally from the sleeve dislodging element of the base member by a distance greater than or equal to a length of the anchor sleeve, when the handle is in the first position; and the collar of the support portion is adjacent to the sleeve dislodging element of the base member, when the handle member is in the second position.

2. In some exemplary embodiments, the handle member further includes a laterally extending tab element configured for engagement by a finger of a hand; and the proximal end of the base member is configured for engagement with another portion of the hand, when the finger engages the tab element of the handle member, the engagement of the hand to slide the handle member from the first position to the second position.

3. Some exemplary embodiments include the tool of statement 1 or 2, wherein the arm of the support portion of the handle member is located on a first side of the base member; and the base member further includes an open channel extending on a second side thereof, between the distal segment and the proximal end, the second side being opposite the first side, the channel being oriented and sized to receive the body of the medical device therein, when the body of the device is received in the collar of the support portion.

4. Some exemplary embodiments include the tool of any of statements 1-3, wherein the sleeve dislodging element of the base member comprises a blade.

5. Some exemplary embodiments include the tool of statement 4, wherein the sleeve dislodging element of the base member further comprises a shroud structure, the shroud structure including a tapered leading edge to slide in between the anchor sleeve and the body of the device, and the blade of the dislodging element being recessed from the tapered leading edge.

6. Some exemplary embodiments include the tool of any of statements 1-3, wherein the sleeve dislodging element of the base member comprises an elongate shroud structure, the shroud structure including a tapered leading edge, and the shroud structure being configured for insertion in between the anchor sleeve and the body of the device along a majority of the length of the anchor sleeve.

7. Some exemplary embodiments include the tool of statement 6, wherein an outer perimeter surface of the shroud structure has a lubricious coating formed thereon, the outer perimeter surface interfacing with an inner surface of the anchor sleeve, when the structure slides in between the anchor sleeve and the body of the device.

8. Some exemplary embodiments include a tool kit for forming a tool according to any of statements 1-7, wherein the body portion of the handle member comprises opposing gripping arms configured to receive the base member therebetween, in a snap-fit to hold the base member in the sliding engagement with the body portion.

9. Some exemplary embodiments of the tool kit of statement 8, wherein the base member includes a marked portion located in proximity to the distal segment thereof, to facilitate alignment and orientation of the base member with the gripping arms of the handle member for the snap-fit, the marked portion corresponding with the first position of the engaged handle member.

10. Some exemplary tool kits comprise a handle member according to any of statements 1-3, and at least two base members, a first base member of the two according to statement 4 or 5, and a second base member of the two according to statement 6 or 7; and wherein: the body portion of the handle member comprises opposing gripping arms configured to receive either the first base member or the second base member therebetween, in a snap-fit to hold the first or second base member in the sliding engagement with the body portion; and the elongate arm of the support portion of the handle member has an adjustable length between a first length and a second length, the first length being approximately equal to the length of the anchor sleeve plus a length of the distal segment of the first base member, and the second length being approximately equal to the length of the anchor sleeve plus a length of the distal segment of the second base member.

11. Some exemplary embodiments of the tool kit of statement 10, wherein each of the two base members includes a marked portion located in proximity to the distal segment thereof, to facilitate alignment and orientation of each base member with the gripping arms of the handle member for the snap-fit, the marked portion corresponding to the first position of the engaged handle member.

The invention claimed is:

1. A tool for dislodging an anchor sleeve from around a body of an implanted elongate medical device, the tool comprising:
   a handle member including a body portion and a support portion, the support portion including an elongate arm extending in a distal direction from the body, the distal direction being parallel to a longitudinal axis, and a collar extending from and terminating a distal end of the elongate arm, the collar defining a first space extending through the collar along the longitudinal axis configured to receive the body of the implanted elongate medical device therethrough, the collar being configured to engage a distal end of the anchor sleeve; and
   an elongate base member held in sliding engagement with the body portion of the handle member, the elongate base member including a distal segment and a proximal end, the distal segment being terminated by a leading edge of a shroud structure defining a sleeve dislodging element, the leading edge directed in the distal direction toward the collar of the support portion of the handle member, the sleeve dislodging element defining a second space along the longitudinal axis configured to receive the body of the implanted elongate medical device therethrough;
   wherein the handle member slides parallel to the longitudinal axis along the elongate base member between:
      a first position with the body portion being in proximity to the distal segment of the elongate base member and the collar of the support portion being spaced in the distal direction from the sleeve dislodging element of the elongate base member to form a distal space along the longitudinal axis between the first and the second spaces for receiving the anchor sleeve therethrough, and
      a second position with the body portion being in proximity to the proximal end of the elongate base member and the collar of the support portion being adjacent to the sleeve dislodging element of the elongate base member.

2. The tool of claim 1, wherein the elongate arm of the support portion of the handle member is located on a first side of the elongate base member; and the elongate base member further includes an open channel extending on a second side thereof, between the distal segment and the proximal end, the second side being opposite the first side, the open channel being oriented and sized to receive the body of the implanted elongate medical device therein, when the body of the implanted elongate medical device is received in the collar of the support portion.

3. The tool of claim 1, wherein the sleeve dislodging element of the elongate base member comprises a blade.

4. The tool of claim 3, wherein the blade of the dislodging element is recessed from the leading edge and the leading edge is tapered.

5. The tool of claim 1, wherein the shroud structure is configured for insertion in between the anchor sleeve and the body of the implanted elongate medical device along a majority of the length of the anchor sleeve.

6. The tool of claim 5, wherein an outer perimeter surface of the shroud structure has a lubricious coating formed thereon, the outer perimeter surface interfacing with an inner surface of the anchor sleeve, when the structure slides in between the anchor sleeve and the body of the implanted elongate medical device.

7. The tool of claim 1, wherein the handle member further includes a laterally extending tab element configured for engagement by a finger of a hand; and the proximal end of the elongate base member is configured for engagement with another portion of the hand, when the finger engages the tab element of the handle member, the engagement of the hand to slide the handle member from the first position to the second position.

8. A tool kit for dislodging an anchor sleeve from around a body of an implanted elongate medical device, the tool comprising:
    a handle member including opposing gripping arms and a support portion, the support portion including an elongate arm extending in a distal direction from the opposing gripping arms, the distal direction being parallel to a longitudinal axis, and a collar extending from and terminating a distal end of the elongate arm, the collar defining a first space extending through the collar along the longitudinal axis, the first space being configured to receive the body of the implanted elongate medical device therethrough, the collar being configured to engage a distal end of the anchor sleeve;
    an elongate base member including a distal segment and a proximal end, the distal segment being terminated by a leading edge of a shroud structure defining a sleeve dislodging element, the sleeve dislodging element defining a second space along the longitudinal axis configured to receive the body of the implanted elongate medical device therethrough;
    wherein the opposing gripping arms of the handle member are configured to receive the elongate base member therebetween, for a snap-fit of the elongate base member with the handle member, the snap-fit holding the handle member in sliding engagement with the elongate base member between:
        a first position with the body portion being in proximity to the distal segment of the elongate base member and the collar of the support portion being spaced in the distal direction from the sleeve dislodging element of the elongate base member to form a distal space along the longitudinal axis between the first and second spaces for receiving the anchor sleeve therethrough, and
        a second position with the body portion being in proximity to the proximal end of the elongate base member and the collar of the support portion being adjacent to the sleeve dislodging element of the elongate base member, the sleeve dislodging element of the elongate base member being directed in the distal direction toward the collar of the support portion of the handle member.

9. The tool kit of claim 8, wherein the elongate base member includes a marked portion located in proximity to the distal segment thereof, to facilitate alignment and orientation of the elongate base member with the opposing gripping arms of the handle member for the snap-fit, the marked portion corresponding to the first position of the engaged handle member.

10. The tool kit of claim 8, wherein the handle member further includes a laterally extending tab element configured for engagement by a finger of a hand; and the proximal end of the elongate base member is configured for engagement with another portion of the hand, when the finger engages the tab element of the engaged handle member, the engagement of the hand with the handle member and elongate base member to slide the engaged handle member from the first position to the second position.

11. The tool kit of claim 8, wherein:
    the elongate base member is a second base member and further comprising a first base member, the sleeve dislodging element of the first base member comprising a blade, the shroud structure being configured to slide in between the anchor sleeve and the body of the implanted elongate medical device along a majority of the length of the anchor sleeve;
    the gripping arms of the handle member are configured to receive either the first base member or the second base member therebetween, for the snap-fit; and
    the elongate arm of the support portion of the handle member has an adjustable length between a first length and a second length, the first length being approximately equal to the length of the anchor sleeve plus a length of the distal segment of the first base member, and the second length being approximately equal to the length of the anchor sleeve plus a length of the distal segment of the second base member.

12. The tool kit of claim 11, wherein the blade of the dislodging element of the first base member is recessed from the leading edge and the leading edge is tapered.

13. The tool kit of claim 8, wherein an outer perimeter surface of the shroud structure of the sleeve dislodging element of the second base member has a lubricious coating formed thereon, the outer perimeter surface interfacing with an inner surface of the anchor sleeve, when the structure slides in between the anchor sleeve and the body of the implanted elongate medical device.

* * * * *